United States Patent
Zhang et al.

(10) Patent No.: US 6,251,430 B1
(45) Date of Patent: *Jun. 26, 2001

(54) WATER INSOLUBLE POLYMER BASED SUSTAINED RELEASE FORMULATION

(76) Inventors: Guohua Zhang, 1 Doric Dr., Parsippany, NJ (US) 07054; Prasad Pinnamaraju, 243 Horizon Dr., Edison, NJ (US) 08817; Muhammad A. Ali, 236 Michelle Cir., Edison, NJ (US) 08820

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/018,522
(22) Filed: Feb. 4, 1998
(51) Int. Cl.$^7$ ....................................... A61K 9/22
(52) U.S. Cl. ................ 424/468; 424/464; 424/474; 424/480; 424/482; 514/964
(58) Field of Search ................... 424/464, 468, 424/474, 480, 482; 514/964

(56) References Cited

U.S. PATENT DOCUMENTS

| | | |
|---|---|---|
| 4,708,874 * | 11/1987 | De Haan et al. . |
| 4,792,452 * | 12/1988 | Howard et al. . |
| 4,966,768 | 10/1990 | Michelucci et al. . |
| 5,132,295 | 7/1992 | Balz et al. . |
| 5,230,901 | 7/1993 | Einig et al. . |
| 5,695,781 * | 12/1997 | Zhang et al. . |
| 6,083,532 * | 7/2000 | Zhang et al. . |

* cited by examiner

Primary Examiner—Thurman K. Page
Assistant Examiner—Brian K. Seidleck
(74) Attorney, Agent, or Firm—Pennie & Edmonds LLP

(57) ABSTRACT

Sustained release drug formulations contain the pharmaceutical itself and a three component release rate controlling matrix composition. The three components of the matrix composition are (1) water insoluble polymer, such as ethyl cellulose, (2) pH dependent gelling polymer, such as sodium alginate, and (3) a pH independent gelling polymer, such as hydroxypropyl methylcellulose. The drug release rate can be adjusted by changing the amount of one or more of these components of the composition.

16 Claims, 3 Drawing Sheets

WATER INSOLUBLE POLYMER BASED SUSTAINED RELEASE FORMULATION

FIELD OF THE INVENTION

Figure 1:
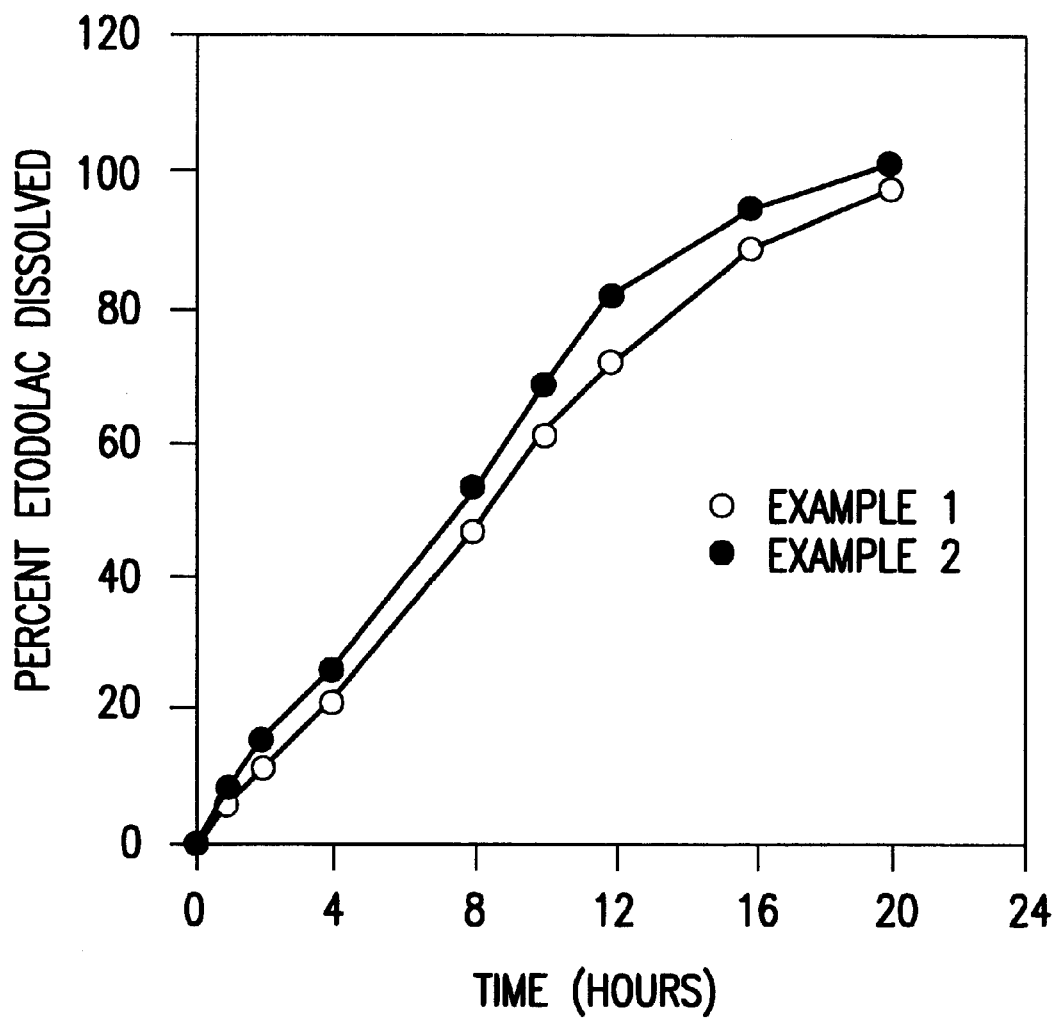

The present invention is directed to formulations for preparing sustained release drug dosage forms useful for releasing pharmaceuticals at controlled rates for oral administration.

BACKGROUND OF THE INVENTION

A controlled release profile from a drug dosage form is sometimes desirable in clinical use to reduce side effects and improve patient compliance. The technology used to formulate sustained release dosage forms is well documented. The entrapment of a drug in a polymer based matrix is a common approach to formulate sustained release tablets with a desirable release profiles.

It has been reported that depot drug formulations for controlled release of pharmaceutical drugs may be prepared using alginates alone (see U.S. Pat. No. 5,132,295), using combinations of alginates and polyacrylates (see U.S. Pat. No. 5,230,901) and using combinations of alginates and a pH independent gelling agent, such as, for example, hydroxypropyl methylcellulose (see U.S. Pat. No. 4,792,452). It is also known that the use of alginates alone for this purpose often presents difficulties in tableting, film coating and storage.

It also has been reported that a sustained release dosage form useful in providing once-a-day medication consists of the admixture of hydroxypropyl methylcellulose (viscosity of 80 to 120 cps in a 2% aqueous solution) and ethylcelluose with etodolac (see U.S. Pat. No. 4,966,768). Using a low viscosity of hydroxypropyl methylcellulose with ethylcellulose as rate controlling agents in the formulation may give a shorter $T_{max}$ (time to peak blood concentration) after oral administration due to a fast tablet erosion.

Adding polyacrylates to the alginate formulation overcomes these difficulties to some extent; however, tablets formed using alginates and polyacrylates often have a pH dependent dissolution profile. In a low pH environment, alginates and polyacrylates do not swell and/or dissolve properly. This leads to drug release by a diffusion mechanism through non-viscous capillaries resulting in a different dissolution rate than in a high pH environment. On the other hand, in a high pH environment, alginates swell and become soluble while polyacrylates may or may not do the same. This leads to drug release both by erosion and diffusion at a rate which is different than the low pH release rate.

In formulations which contain an alginate and a pH independent gelling polymer such as, for example, hydroxypropyl methylcellulose, hydration at low pH levels forming a viscous gel layer for drug release. At high pH levels, however, tablets become smaller and smaller during drug release due to erosion of the swollen polymer layer, leading to a reduction in surface area which may affect the dissolution rate of a tablet.

The novelty of the present invention is the provision of a sustained release formulation which reduces, and perhaps eliminates the aforementioned problems completely. In particular the invention provides a controlled release drug formulation which includes novel formulations containing three different types of polymers. These three different types of polymers include: 1) a water insoluble polymer, such as ethylcellulose; 2) a pH independent gelling polymer, such as hydroxypropyl methylcellulose; and 3) a pH dependent gelling polymer, such as sodium alginate. These three different types of polymers must be used together to achieve a controlled release rate of the selected drug. Such a combination of polymers facilitates manufacturing processes and improves drug release and absorption profiles.

In accordance with the present invention, the combination of the three polymers provides an excellent matrix drug depot system with desirable controlled release characteristics. During dissolution at low pH levels, such as in the stomach, the pH independent gelling polymer e.g., hydroxypropyl methylcellulose, hydrates and swells to form a hydrogel which controls drug release from the matrix system. Drug release may be due to the gel layer erosion or drug diffusion through the gel layer or a combination of both. The water insoluble polymer e.g., ethylcellulose, and the pH dependent gelling polymer e.g., sodium alginate, are dispersed in the gel layer as insoluble parties to block the diffusion pathway or adjust the erosion rate of the gel layer. All the three polymers play important roles to control drug release at a low pH environment. As the matrix system moves to a higher pH environment e.g. in the intestinal tract, the tablet surface area becomes smaller due to the gel layer erosion, which may lead to a reduction of drug release rate. However, the pH dependent gelling polymer dispersed in the gel layer starts to hydrate and swell. Meanwhile, the insoluble particles dispersed in the gel layer will be reduced due to the hydration of pH dependent gelling polymer, resulting of the opening of additional diffusion channels. Therefore, hydration of the pH dependent polymer and concomitant reduction of the insoluble particles in the hydrogel in high pH environment, will compensate the reduction tendency of the drug release rate due to the surface area changes resulting from erosion. Thus, drug release rate is maintained regardless of the pH and tablet size changes. Thus, the formulations of the present invention provide improved drug release profiles compared with the prior art formulations described above.

BRIEF DESCRIPTION OF THE DRAWING FIGURES

FIG. 1 demonstrates the sustained drug release profiles of the formulations in Examples 1 and 2.

Figure 2:
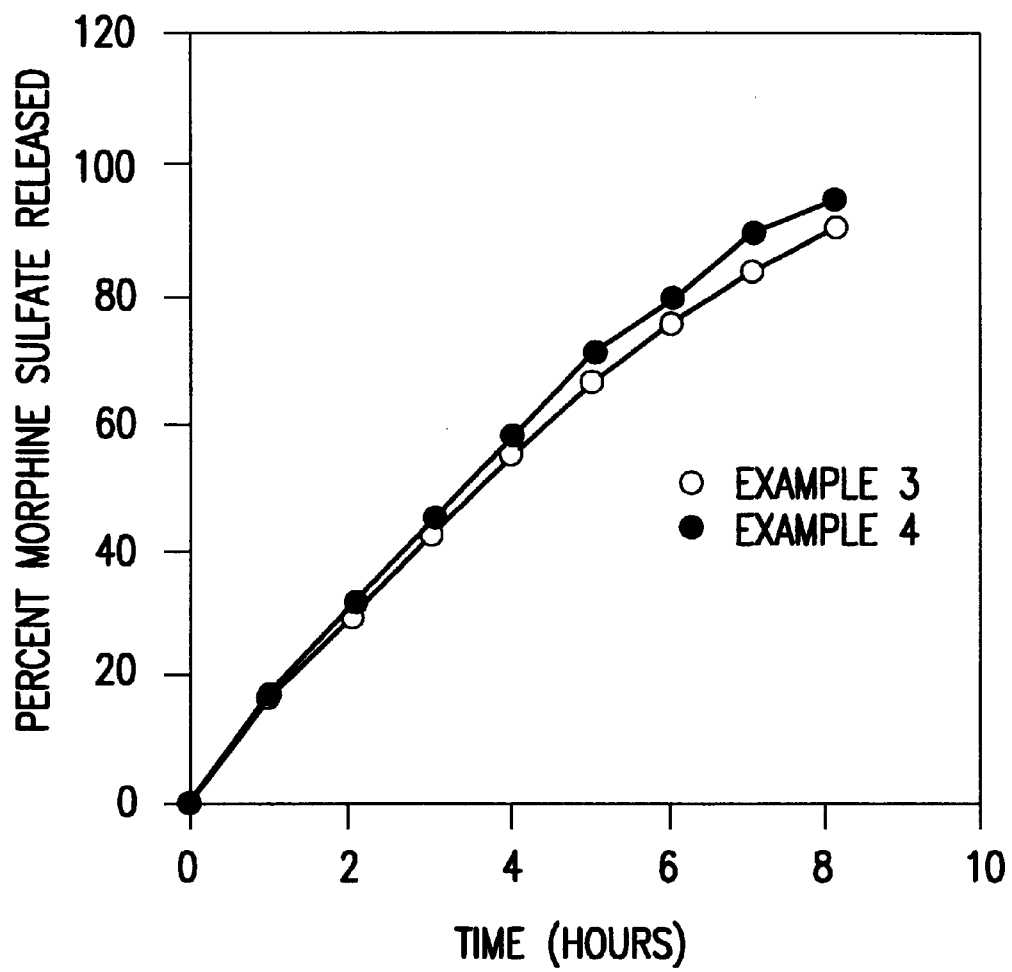

FIG. 2 demonstrates the sustained drug release profiles of the formulations in Examples 3 and 4.

Figure 3:
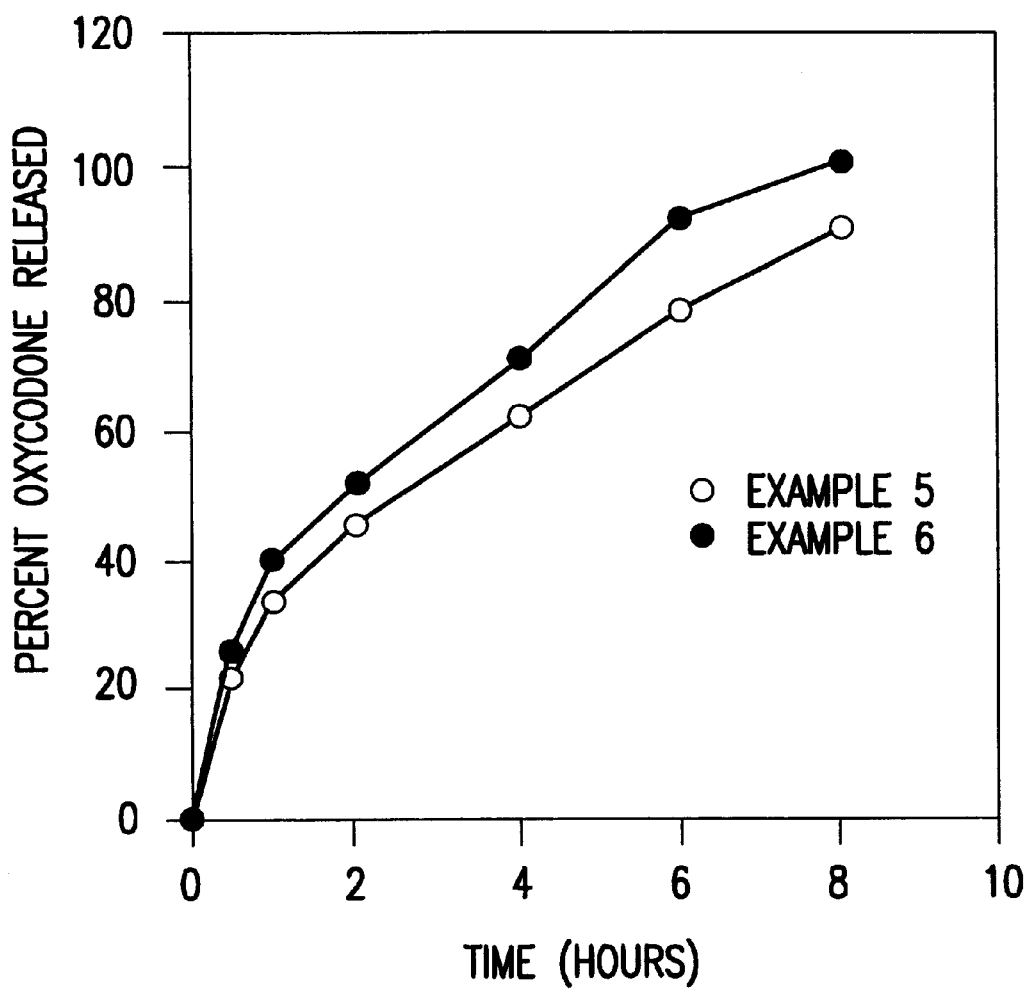

FIG. 3 demonstrates the sustained drug release profiles of the formulations in Examples 5 and 6.

DETAILED DESCRIPTION OF THE PREFERRED EMBODIMENTS

The present invention provides sustained release tablets formulated with a mixture of three different types of polymers; a water insoluble polymer, a pH dependent gelling polymer and pH independent gelling polymer, from which the pharmaceutical active may be released at a controlled rate.

One or more suitable water insoluble polymers may be selected to be used in the invention, which include, but are not limited to, ethylcellulose and co-polymers of acrylic and methacrylic acid esters (Eudragit® RS or RL). One or more suitable pH dependent gelling polymer may be selected to be used in the invention, which includes, but not limited to, alginates and sodium carboxymethylcellulose. One or more suitable pH independent gelling polymers may be selected to be used in the invention, which include, but are not limited to, carboxypolymethylene, hydrxpropyl methylcellulose, hydroxypropyl cellulose, hydroxypropyl ethylcellulose, hydroxyethylcellulose, methylcellulose, xanthum gum and polyethylene oxide.

Suitable pharmaceutical compositions include those having an active ingredient selected from the group consisting of antihistamines, antibiotics, antituberculocis agents, cholinergic agents, antimuscarinics, sympathominetics, sympatholytic agents, autonomic drugs, iron preparations, haemostatics, cardiac drug, antiinflammatory agents, opiate agonists, anticonvulsants, tranquilizers, stimulants, barbiturates, sedatives, expectorants, antiemetics, gastrointestinal drugs, heavy metal antagonists, antithyroid agents, genitourinary smooth muscle relaxants and vitamins. The invention is applicable to active ingredients regardless of their solubility.

The overall tablet formulation should include a mixture of three types of polymers in an amount so as to establish a weight percentage of from about 6% to about 60% based on the total tablet weight, preferably from about 10% to about 50% in the formulation. The three type of polymers should include 1) water insoluble polymer in an amount of from 2% to 30% of the total tablets weight, preferably from about 3% to about 25%; 2) pH dependent gelling polymer in an amount of from about 2% to about 40% of the total tablet weight, preferably from about 3% to about 30%; and 3) pH independent gelling in an amount of from about 2% to about 30%, preferably from about 3% to about 25%.

In a preferred form, the formulation of the invention should contain 1) water insoluble polymer component, such as ethylcellulose; 2) pH dependent gelling polymer, such as sodium alginate, having a viscosity range of from about 50–10,000 centipoises in a 2% by weight water solution at 25° C., preferably from about 100 to about 7,000 centipoises, measured using a Brookfield LV viscometer; and 3) pH independent gelling polymer, such as hydroxypropyl methylcellulose, having a viscosity range of from about 50 to about 150,000 centipoises, preferably from about 200 to about 120,000 centipoises in a 2% by weight water solution at 25° C., measured using a Brookfield LV viscometer.

Other ingredients which may be optionally included in the formulation of the invention are: 1) tablet filler; 2) binder; 3) lubricant; 4) colorant, and 5) film forming polymer for coating. The amounts of all these common ingredients selected in the formulation should be in a pharmaceutically acceptable range.

The following examples are set forth to illustrate the claimed invention and are not to be construed as a limitation thereof.

Specific Examples of the Preferred Embodiments

| Ingredient | | |
|---|---|---|
| | Example 1 | Example 2 |
| Etodolac | 400.0 mg | 400.0 mg |
| Ethylcellulose (Ethocel 10 FP) | 80.0 mg | — |
| Co-Polymer of Acrylic and Methacrylic Acid Ester (Eudragit ® RS) | — | 60.0 mg |
| Hydroxypropyl Methylcellulose (Methocel K100M) | 40.0 mg | — |
| Hydroxyethylcellulose (Natrosol 250 HX) | — | 80.0 mg |
| Sodium Alginate (Keltone HVCR) | 70.0 mg | 80.0 mg |
| Lactose | 86.4 mg | 66.4 mg |

-continued

Specific Examples of the Preferred Embodiments

| Ingredient | | |
|---|---|---|
| Microcrystalline cellulose ((Avicel PH 101) | 40.0 mg | 30.0 mg |
| Magnesium stearate | 3.6 mg | 3.6 mg |
| | Example 3 | Example 4 |
| Morphine Sulfate | 100.0 mg | 60.0 mg |
| Ethylcellulose (Ethocel 10 FP) | 25.0 mg | — |
| Co-Polymer of Acrylic and Methacrylic Acid Esters (Eudragit ® RS) | — | 20.0 mg |
| Hydroxyproyl Methylcellulose (Methocel K4M) | 15.0 mg | — |
| Hydroxyethylcellulose (Natrosol 250 HX) | — | 25.0 mg |
| Sodium Alginate (Keltone LVCR) | 25.0 mg | 40.0 mg |
| Lactose | 14.0 mg | 34.0 mg |
| Microcrystalline cellulose (Avicel PH 101) | 20.0 mg | 20.0 mg |
| Magnesium stearate | 1.0 mg | 1.0 mg |
| | Example 5 | Example 6 |
| Oxycodone Hydrochloride | 40.0 mg | 20.0 mg |
| Ethylcellulose (Ethocel 10 FP) | — | 10.0 mg |
| Co-Polymer of Acrylic and Methacrylic Acid Esters (Eudragit ® RS) | 10.0 mg | — |
| Hydroxypropyl Methylcellulose (Methocel K4M) | 20.0 mg | — |
| Hydroxyethylcellulose (Natrosol 250 HX) | — | 20.0 mg |
| Sodium Alginate Keltone LVCR) | 40.0 mg | 40.0 mg |
| Lactose | 35.0 mg | 55.0 mg |
| Microcrystalline cellulose (Avicel PH 101) | 4.0 mg | 4.0 mg |
| Magnesium stearate | 1.0 | 1.0 mg |

In this invention, Ethylcellulose is National Formulary ("NF") grade with the trademark of Ethocel or equivalent. Hydroxypropyl methylcellulose is United States Pharmacopeia ("USP") grade with the trademark of Methocel or equivalent. Hydroxyethylcellulose is NF grade with the trademark of Natrosol or equivalent. The co-polymer of acrylic and methacrylic acid esters is the NF grade with the trademark of Eudragit or equivalent. Sodium alginate is the NF grade with the trademark of Keltone or equivalent.

FIGS. 1 to 3 demonstrate drug release profiles for each example discussed above. The dissolution tests were performed in simulated intestinal fluid (0.1 N HCl) using USP dissolution test method II (paddle methods).

All ingredients are mixed except magnesium stearate in a mixer such as a high shear mixer granulator or planetary mixer to obtain homogeneity. The mixture is then granulated using water or other suitable granulation fluids and dried in a dryer. The dried granulation is then milled, followed by lubrication by mixing the granules with magnesium stearate. The lubricated granulation is then compressed into tablets using a tablet press. The foregoing steps are conventional steps used in the pharmaceutical industry.

In the preferred embodiments set forth above, the formulations of the invention have particular utility in preparation of sustained release tablets of etodolac, morphine sulfate and oxycodone hydrochloride. However, the invention is not limited to use in connection with these three drugs only. Tablets containing other drugs requiring sustained release are within the intended scope of the invention. Additionally, drugs suitable for this invention are water-soluble or water-insoluble.

Those skilled in the art will recognize, or be able to ascertain using no more than routine experimentation, many equivalents to specific embodiments of the invention described herein. Such equivalents are intended to be encompassed in the scope of the following claims.

We claim:

1. A sustained release tablet comprising an effective amount of a drug to be released at a controlled rate and a homogenous mixture of three different types of polymers including a water insoluble polymer compound, a pH dependent gelling polymer, and a pH independent gelling polymer, wherein said water insoluble polymer comprises one or more of ethylcellulose and co-polymers of acrylic and methacrylic acid esters.

2. A sustained release tablet of claim 1 comprising effective amounts of said water insoluble polymer compound, pH independent gelling polymer, and pH dependent gelling polymer to control the release of said rate drug.

3. A tablet of claim 2 wherein said effective amount of pH dependent gelling polymer does not hydrate over the pH range in the stomach but hydrates over the pH range in the intestine controlling said release rate of said drug.

4. A tablet of claim 2 wherein said effective amount of pH independent gelling polymer hydrates in the stomach and intestine to control said release rate of said drug.

5. A tablet of claim 2, wherein said pH independent gelling polymer comprises one or more of hydroxypropyl methylcellulose, hydroxypropyl cellulose, hydroxyethyl cellulose, hydroxypropyl ethylcellulose, methylcellulose, xanthum gum, polyethylene oxide and carboxypolymethylene.

6. A tablet of claim 2, wherein said pH dependent gelling polymer comprises one or more of sodium alginate and sodium carboxymethylcellulose.

7. A tablet of claim 5, wherein said pH independent gelling polymer has a viscosity within the range from about 50 to about 150,000 centipoises in a 2% by weight aqueous solution, measured using a Brookfield LV viscometer.

8. A tablet of claim 6 wherein said pH dependent gelling polymer has a viscosity within the range from about 50 to about 10,000 centipoises in a 2% by weight aqueous solution, measured using a Brookfield LV viscometer.

9. A method of forming a sustained release depot drug dosage form comprising introducing an effective amount of a drug in a tablet comprising and from about 6 to about 60 percent by weight of a homogenous mixture of three different types of polymers including water insoluble polymer compound, a pH independent gelling polymer, and a pH dependent gelling polymer, wherein said water insoluble polymer comprises one or more of ethylcellulose and co-polymers of acrylic and methacrylic acid esters.

10. A tablet of claim 1, wherein said water insoluble polymer is from about 2% to about 30% of the tablet weight.

11. A tablet of claim 1, wherein said pH dependent gelling polymer is from about 2% to about 40 % of the tablet weight.

12. A tablet of claim 1, wherein said pH independent gelling polymer is from about 2% to about 30% of the tablet weight.

13. A tablet of claim 1, wherein said drug is etodolac.

14. A tablet of claim 1, wherein said drug is morphine sulfate.

15. A tablet of claim 1, wherein said drug is oxycodone hydrochloride.

16. A tablet of claim 1, wherein said drug is water soluble or water sparingly soluble, or water insoluble.

* * * * *